(12) United States Patent
Chen et al.

(10) Patent No.: US 10,882,830 B2
(45) Date of Patent: Jan. 5, 2021

(54) CRYSTAL FORM OF OZANIMOD HYDROCHLORIDE AND PROCESSES FOR PREPARATION THEREFOR

(71) Applicant: Receptos LLC, New York, NY (US)

(72) Inventors: Minhua Chen, Jiangsu (CN); Yanfeng Zhang, Jiangsu (CN); Xiaoting Zhai, Jiangsu (CN); Kaiqiang Yan, Jiangsu (CN); Chaohui Yang, Jiangsu (CN); Xiaoyu Zhang, Jiangsu (CN)

(73) Assignee: RECEPTOS LLC, New York, NY (US)

( * ) Notice: Subject to any disclaimer, the term of this patent is extended or adjusted under 35 U.S.C. 154(b) by 0 days.

(21) Appl. No.: 16/333,075

(22) PCT Filed: Sep. 14, 2017

(86) PCT No.: PCT/CN2017/101737
§ 371 (c)(1),
(2) Date: Mar. 13, 2019

(87) PCT Pub. No.: WO2018/050091
PCT Pub. Date: Mar. 22, 2018

(65) Prior Publication Data
US 2019/0248755 A1    Aug. 15, 2019

(30) Foreign Application Priority Data
Sep. 14, 2016 (CN) ............... 2016 1 0822328

(51) Int. Cl.
| | | |
|---|---|---|
| C07D 273/02 | (2006.01) |
| A61K 31/41 | (2006.01) |
| A61K 31/425 | (2006.01) |
| A61P 37/00 | (2006.01) |
| A61K 9/00 | (2006.01) |
| C07D 271/06 | (2006.01) |
| A61P 37/02 | (2006.01) |
| A61P 1/04 | (2006.01) |

(52) U.S. Cl.
CPC .............. *C07D 273/02* (2013.01); *A61K 9/00* (2013.01); *A61K 31/41* (2013.01); *A61K 31/425* (2013.01); *A61P 1/04* (2018.01); *A61P 37/00* (2018.01); *A61P 37/02* (2018.01); *C07D 271/06* (2013.01); *C07B 2200/13* (2013.01)

(58) Field of Classification Search
CPC .................................................. C07D 273/02
See application file for complete search history.

(56) References Cited

U.S. PATENT DOCUMENTS

| | | | | |
|---|---|---|---|---|
| 2011/0172202 | A1* | 7/2011 | Martinborough | A61P 37/06 514/210.18 |
| 2019/0337908 | A1 | 11/2019 | Chen et al. | |
| 2020/0031784 | A1* | 1/2020 | Sheng | A61P 37/00 |
| 2020/0157065 | A1 | 5/2020 | Chen et al. | |

FOREIGN PATENT DOCUMENTS

| | | |
|---|---|---|
| CN | 102118972 A | 7/2011 |
| CN | 102762100 A | 10/2012 |
| CN | 107840830 A | 3/2018 |
| WO | 2009/151529 A1 | 12/2009 |
| WO | 2011/060392 A1 | 5/2011 |
| WO | 2015/066515 A1 | 5/2015 |
| WO | 2016/164180 A1 | 10/2016 |
| WO | 2017/215617 A1 | 12/2017 |
| WO | 2018/049632 A1 | 3/2018 |
| WO | 2018/050091 A1 | 3/2018 |

OTHER PUBLICATIONS

Huan, Shijie, Journal of InternationalPharmaceutical Research, Aug. 31, 2016, vol. 43, p. 786.
Jiang, Zhi, et al., Research and Development of Sphingosine 1-Phospate Modulators, Progress in Pharmaceutical Sciences Jul. 31, 2016, vol. 40 (7), p. 548-554.
S. Byrn, et al., Pharmaceutical Research, vol. 12, No. 7, p. 945-954 (1995).
F.L. Scott, et al., British Journal of Pharmacology 173, p. 1778-1792 (2016).
U.S. Appl. No. 16/310,328, filed Dec. 14, 2018, 2019-0337908, Published.
U.S. Appl. No. 16/748,303, filed Jan. 21, 2020, 2020-0157065, Published.
U.S. Appl. No. 16/326,353, filed Feb. 18, 2019, Pending.
U.S. Appl. No. 16/643,011, filed Feb. 28, 2020, Pending.
Caira, Crystalline Polymorphism of Organic Compounds. Topics in Current Chemistry. 1998;198;163-208.
Jacob et al., Solid State Crystallinity, Amorphous State, and Its Implications in the Pharmaceutical Process. IJPSR, Feb. 2011(3):472-482.
International Search Report and Written Opinion for Application No. PCT/CN2017/088314, dated Aug. 30, 2017, 13 pages.
(Continued)

*Primary Examiner* — Matthew P Coughlin
(74) *Attorney, Agent, or Firm* — McCarter & English, LLP; Wei Song (57) ABSTRACT

The present disclosure relates to crystalline form CS3 of ozanimod hydrochloride which can be used for treating autoimmune diseases, particularly used for preparing drugs for treating multiple sclerosis and ulcerative colitis and preparation method thereof.

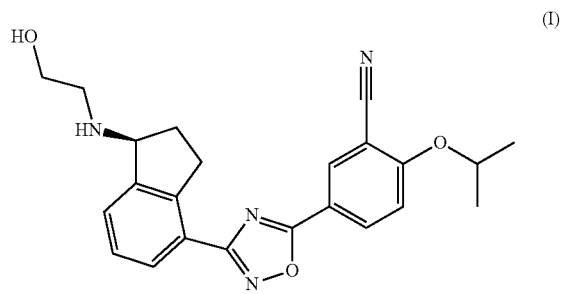

12 Claims, 4 Drawing Sheets

(56) References Cited

OTHER PUBLICATIONS

International Search Report and Written Opinion for Application No. PCT/CN2018/102034, dated Nov. 29, 2018, 11 pages.
Campeta et al., Development of a targeted polymorph screening approach for a complex polymorphic and highly solvating API. J Pharm Sci. Sep. 2010;99(9):3874-86.

* cited by examiner

CRYSTAL FORM OF OZANIMOD HYDROCHLORIDE AND PROCESSES FOR PREPARATION THEREFOR

This application is a U.S. national stage application of the PCT International Application No. PCT/CN2017/101737 filed on Sep. 14, 2017, which claims the benefit of foreign priority of Chinese patent application No. 201610822328.0 filed on Sep. 14, 2016.

TECHNICAL FIELD

The present disclosure relates to the field of pharmaceutical chemistry, particularly relates to crystalline form of ozanimod hydrochloride and process for preparation thereof.

BACKGROUND

Multiple sclerosis is the most common primary demyelinating disease that affects the central nervous system. Multiple sclerosis can cause a variety of symptoms, including changes in sensation, visual problems, muscle weakness, depression, difficulties with coordination and speech, severe fatigue, cognitive impairment, balance problem, body heat and pain. Serve multiple sclerosis can lead to movement disorder and disabilities. Multiple sclerosis lesions are located in the brain or spinal cord and multiple sclerosis gradually causes the plaque damage of the nerve myelin sheath of brain and spinal cord (demyelination). Myelin sheath scar can affect the signal transmission of the nerve axons, and the control over the outer periphery of the brain and the spinal cord is lost, so that stiffness or losses of function of multiple parts are happened. Globally, multiple sclerosis affects about 2.3 million people, with an average age of 20-40 years. The pathogenesis of multiple sclerosis is not clear. Multiple sclerosis is considered as an autoimmune disease, and an effective radical treatment method is not available at present.

Sphingosine-1-phosphate family members participate in numerous important cell physiological processes, such as cell proliferation, angiogenesis, immune cell trafficking, etc. The sphingosine-1-phosphate receptors (S1PR) are a class of G protein-coupled receptors, which can regulate a variety of downstream signaling molecules and cellular functions and have already been considered as a novel relative target molecule used for regulating various diseases (such as multiple sclerosis, lung cancer, psoriasis, kidney injury, uremia and pain). Fingolimod is the first S1PR protein modulator and the first oral regulatory drug for multiple sclerosis, which was approved by the FDA in the United States in 2010.

Ozanimod is a novel, oral, selective modulator of S1PR developed by Receptos for the treatment of autoimmune diseases, especially for the treatment of multiple sclerosis and ulcerative colitis having a significant effect. In clinical trials, ozanimod's clinical results showed better safety data than fingolimod, especially when it comes to heart safety. Ozanimod has very excellent pharmacokinetics, efficacy and safety data in clinical trials, which can perfectly meet the differentiated development strategy and is expected to be the best second-generation S1PR modulator drug. The chemical structure of the drug is shown as formula (I) and it is an S-enantiomer.

Different crystalline forms of the same solid chemical drug are significantly different in solubility, stability, fluidity, compressibility and the like, which can in turn affect the safety and efficacy of the drug products (refer to K. Knapman, Modern Drug Discovery, 3, 53-54, 57, 2000.) and leads to differences in clinical efficacy. Until now, there is no solid form or crystalline form of ozanimod disclosed in the prior art. Therefore, it is necessary to perform comprehensive polymorph screening of ozanimod to select a crystalline form suitable for drug development.

The inventors of the present disclosure have found three crystalline forms of ozanimod hydrochloride through research studies, which provides new choices for the preparation of ozanimod drug product.

SUMMARY

According to the objective of the present disclosure, crystalline form CS3 of ozanimod hydrochloride is provided (hereinafter referred to as Form CS3).

The X-ray powder diffraction pattern of Form CS3 shows characteristic peaks at 2 theta values of 19.6°±0.2°, 24.9°±0.2° and 5.8°±0.2° using CuKα radiation.

Furthermore, the X-ray powder diffraction pattern of Form CS3 shows one or two or three diffraction peaks at 2 theta values of 7.8°±0.2°, 11.7°±0.2° and 29.5°±0.2°. Preferably, the X-ray powder diffraction pattern of Form CS3 shows diffraction peaks at 2 theta values of 7.8°±0.2°, 11.7°±0.2° and 29.5°±0.2°.

Furthermore, the X-ray powder diffraction pattern of Form CS3 shows one or two or three characteristic peaks at 2 theta values of 3.9°±0.2°, 14.2°±0.2° and 20.7°±0.2°. Preferably, the X-ray powder diffraction pattern of Form CS3 shows diffraction peaks at 2 theta values of 3.9°±0.2°, 14.2°±0.2° and 20.7°±0.2°.

In a preferred embodiment, the X-ray powder diffraction pattern of Form CS3 shows characteristic peaks at 2 theta values of 19.6°±0.2°, 24.9°±0.2°, 5.8°±0.2°, 7.8°±0.2°, 11.7°±0.2°, 29.5°±0.2°, 3.9°±0.2°, 14.2°±0.2° and 20.7°±0.2°.

Figure 1:
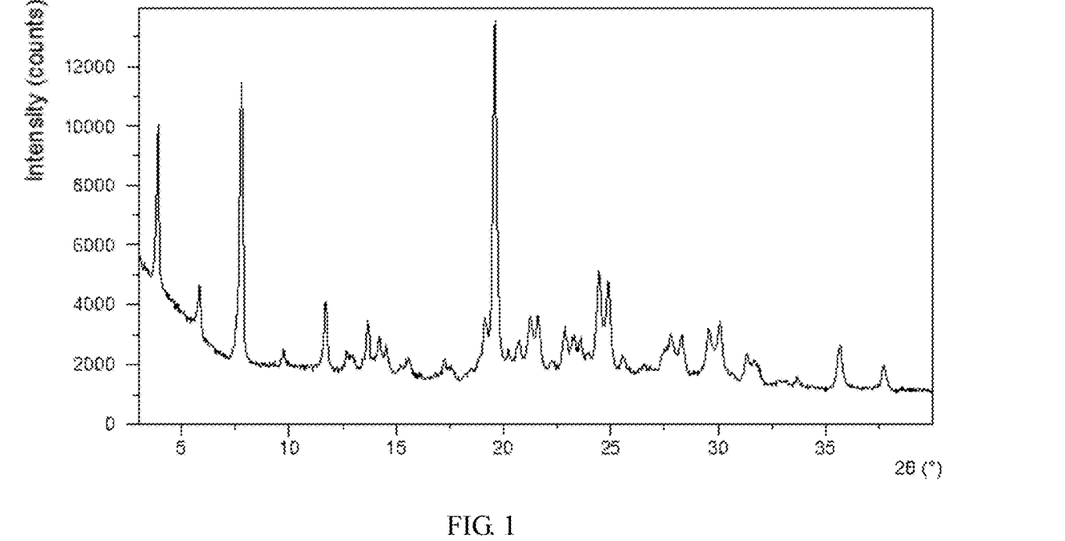
FIG. 1 shows an XRPD pattern of Form CS3 in Example 1

Without any limitation being implied, in a preferred embodiment, the X-ray powder diffraction pattern of Form CS3 is substantially as depicted in FIG. 1.

According to the objective of the present disclosure, the present disclosure further provides the process for preparing Form CS3. The process comprises: dissolving ozanimod hydrochloride into ethanol or a mixture of solvents selected from alcohols and arenes, alcohols and nitriles, alcohols and acids, acids and water, filtering and adding polymer into the solution and then evaporating at room temperature to obtain white solid.

Said alcohols are preferably methanol and ethanol; said acid is preferably acetic acid; said arenes include toluene; said nitriles include acetonitrile.

Another objective of the present disclosure is to provide a pharmaceutical composition comprising a therapeutically amount of Form CS3 and pharmaceutically acceptable carriers, diluents or excipients.

Form CS3 provided by the present disclosure can be used for preparing drugs of selective modulator of sphingosine-1-phosphate receptor.

Form CS3 provided by the present disclosure can be used for preparing drugs for treating ulcerative colitis.

Form CS3 provided by the present disclosure can be used for preparing drugs for treating multiple sclerosis.

Said "room temperature" in the present disclosure is not an exact temperature value and refers to 10-30° C.

Said "stirring" is accomplished by using a conventional method in the field such as a magnetic stirring or a mechanical stirring and the stirring speed is 50 to 1800 r/min, preferably is 300 to 900 r/min.

Said "separation" is accomplished by using a conventional method in the field such as centrifugation or filtration. The operation of "centrifugation" is as follows: the sample to be separated is placed into the centrifuge tube, and then centrifuged at a rate of 10000 r/min until the solid all sink to the bottom of the tube.

Said "drying" is accomplished at room temperature or a higher temperature. The drying temperature is from room temperature to about 60° C., or to 40° C., or to 50° C. The drying time can be 2 to 48 hours, or overnight. Drying is accomplished in a fume hood, oven or vacuum oven.

Said "evaporating" is accomplished by using a conventional method in the field. For example, slow evaporation is to seal the container with a sealing film and puncture holes for evaporation. Rapid evaporation is to place the container open for evaporation.

Said "polymer" is a mixture of equal masses of polycaprolactone, polyoxyethylene, polymethyl methacrylate, sodium alginate, and hydroxyethyl cellulose.

The beneficial effects of the present disclosure are as follows:

At present, no patent or literature has disclosed the crystalline form of ozanimod hydrochloride and inventors of the present disclosure broke through this difficult problem and found several novel crystalline forms of ozanimod suitable for drug development.

Solubility is one of the key characteristics of a drug, which directly affects in vivo absorption of the drug. Different crystalline forms have remarkable different solubility, and will affect in vivo absorption, thus lead to differences in bioavailability. As a result, clinical safety and efficacy will be affected. Form CS3 of present disclosure has good solubility in water, SGF (simulated gastric fluids) and FeSSIF (fed state simulated intestinal fluids).

Stability plays an important role in judging whether a crystalline form has development value. Especially during the commercial shelf life, maintaining stable can reduce the change of drug dissolution rate and bioavailability due to crystal transformation, which is of great significance to ensure the efficacy and safety of the drug and prevent the occurrence of adverse drug reactions. Samples of Form CS3 of the present disclosure are placed under the conditions of 25° C./60% RH and 40° C./75% RH for a period of time. The crystalline form doesn't change, showing that Form CS3 has good stability.

The crystalline form of hydrochloride provided by the present disclosure has advantages in solubility, hygroscopicity, stability, etc. Form CS3 of the present disclosure have uniform particle size distribution and good dispersion, which simplifies the post-process for preparation and provides a new and better choice for the preparation of drugs containing ozanimod and is of great significance for drug development.

DETAILED DESCRIPTION OF THE DISCLOSURE

The present disclosure is further illustrated by the following examples in detail, but is not intended to limit the scope of the present disclosure. The skilled in the art can make improvements to the process of preparation and the instruments used within the scope of the claims, and those improvements should be considered as falling into the scope of the present disclosure. Therefore, the protective scope of the present disclosure patent should be defined by the claims.

In the following examples, the test method is generally implemented according to a conventional condition or a condition recommended by manufacturer.

The abbreviations used in the disclosure are explained as follows:

XRPD: X-ray Powder Diffraction

DSC: Differential Scanning calorimetry

TGA: Thermal Gravimetric Analysis

DVS: Dynamic Vapor Sorption

PSD: Particle Size Distribution

PLM: Polarized Light microscopy

X-ray powder diffraction pattern in the present disclosure was acquired by a Panalytical Empyrean X-ray powder diffractometer. The parameters of the X-ray powder diffraction method of the present disclosure were as follows:

X-ray Reflection: Cu, Kα

Kα1 (Å): 1.540598; Kα2 (A): 1.544426

Kα2/Kα1 intensity ratio: 0.50

Voltage: 45 (kV)

Current: 40 (mA)

Scan range: from 3.0 degree to 40.0 degree

Differential scanning calorimetry (DSC) data in the present disclosure were acquired by a TA Q2000. The parameters of the differential scanning calorimetry (DSC) method of the present disclosure were as follow:

Heating rate: 10° C./min

Purge gas: nitrogen

Thermal gravimetric analysis (TGA) data in the present disclosure were acquired by a TA Q500. The parameters of the thermal gravimetric analysis (TGA) method of the present disclosure were as follow:

Heating rate: 10° C./min

Purge gas: nitrogen

Dynamic Vapor Sorption (DVS) is measured via an SMS (Surface Measurement Systems Ltd.) intrinsic DVS. Typical Parameters for DVS test are as follows:

Temperature: 25° C.
Gas and flow rate: $N_2$, 200 mL/min
dm/dt: 0.002%/min
RH range: 0% RH to 95% RH The particle size distribution test in the present disclosure is acquired by the S3500 laser particle size analyzer of Microtrac. Microtrac S3500 is equipped with the SDC (Sample Delivery Controller). The test is carried out by wet process, and the dispersion medium is Isopar G The parameters are as follow:

| | |
|---|---|
| Size distribution: Volume | Run Time: 10 s |
| Dispersion medium: Isopar G | Particle coordinates: Standard |
| Run Number: Average of 3 runs | Fluid refractive index: 1.42 |
| Particle Transparency: Trans | Residuals: Enabled |
| Particle refractive index: 1.5 | Flow rate: 60%* |
| Particle shape: Irregular | Filtration: Enabled |
| Ultrasonication power: 30 W | Ultrasonication time: 30 s |

*Flow rate 60% is 60% of 65 mL/s.

Raw materials of ozanimod and/or a salt thereof used in the following examples are prepared by methods disclosed in CN102762100A.

Example 1

Preparation of Form CS3 of Ozanimod Hydrochloride

Certain amount of ozanimod hydrochloride solid was weighed into a 3.0-mL glass vial, and corresponding volume of solvent in Table 1 was added to dissolve the solid. Then the mixture was filtered and approximately 0.2 mg of polymer was added into the clear solution, and then the mixture was evaporated slowly at room temperature to obtain white solid.

TABLE 1

| Sample | Weight (mg) | Solvent (v:v) | Volume (mL) |
|---|---|---|---|
| 1-a | 20.3 | Methanol/Ethyl acetate 3:1 | 6.0 |
| 1-b | 5.0 | Ethanol | 1.6 |
| 1-c | 5.3 | Acetic acid/Water 9:1 | 0.5 |
| 1-d | 5.3 | Methanol/Toluene 3:1 | 0.5 |
| 1-e | 5.3 | Methanol/Acetic acid 1:1 | 0.8 |
| 1-f | 5.0 | Methanol/Acetonitrile 2:1 | 0.5 |

Figure 2:
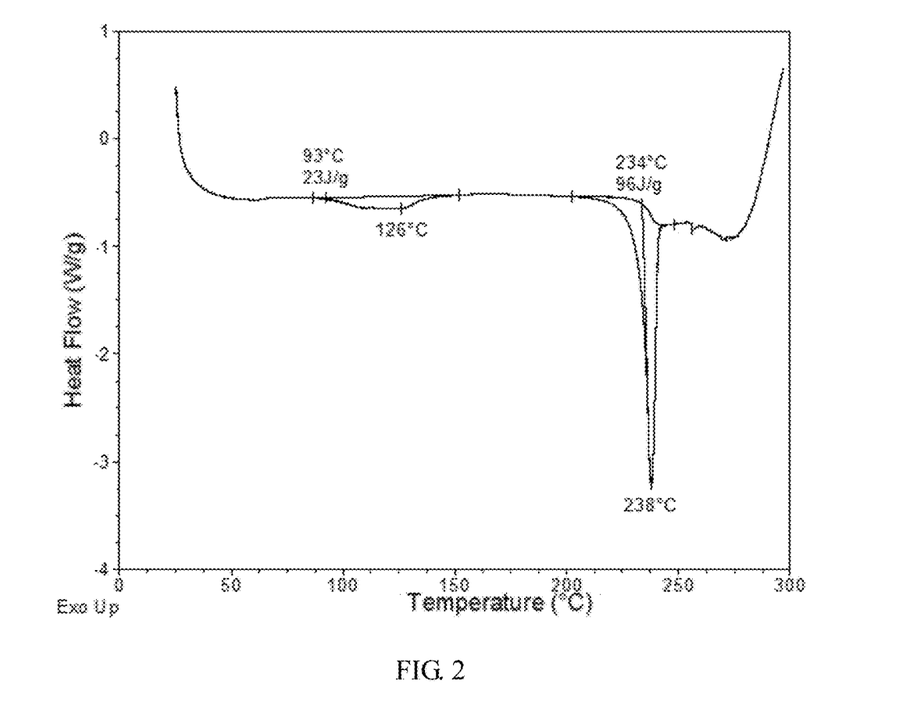
FIG. 2 shows a DSC curve of Form CS3 in Example 1
Figure 3:
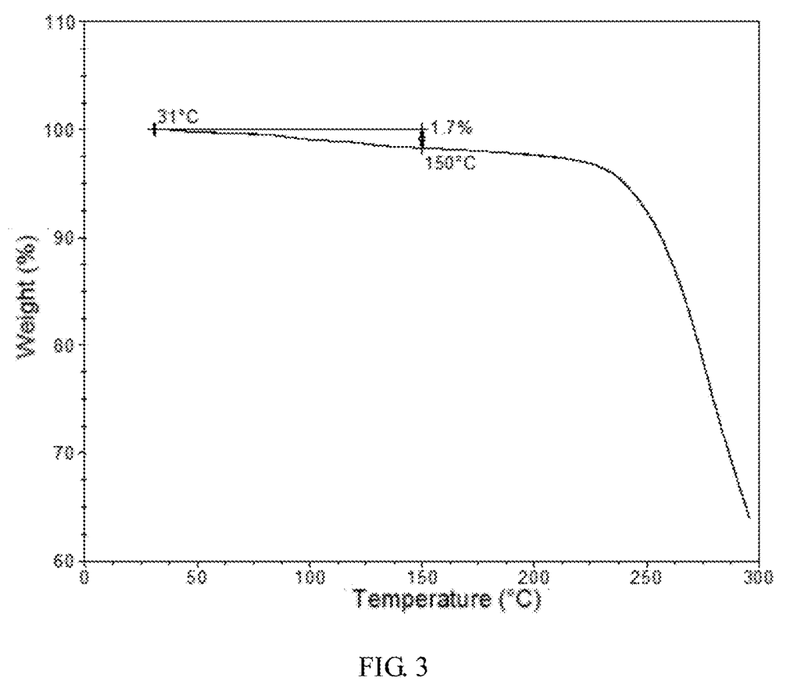
FIG. 3 shows a TGA curve of Form CS3 in Example 1
Figure 4:
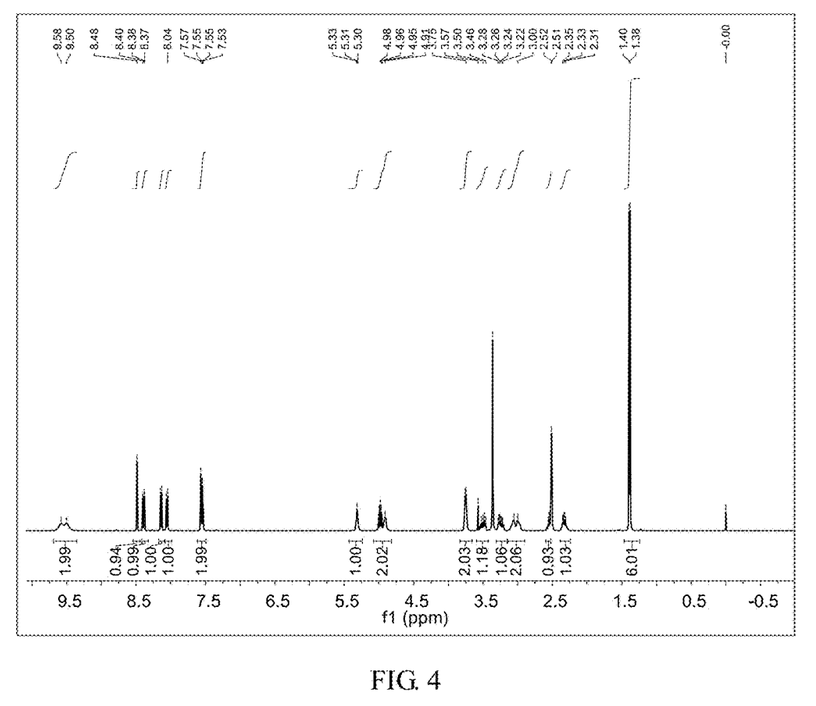
FIG. 4 shows a $^1$H NMR spectrum of Form CS3 in Example 1

The obtained solids were confirmed to be Form CS3. The XRPD data of the solid obtained in example 1-a are listed in Table 2. The XRPD pattern is substantially as depicted displayed in FIG. 1. The DSC curve shows the first endothermic peak when heated to around 93° C., and shows the second endothermic peak when heated to around 234° C., which is substantially as depicted in FIG. 2. The TGA curve of Form CS3 shows about 1.7% weight loss when heated to 150° C., which is substantially as depicted in FIG. 3. The $^1$H NMR spectrum of the solid is substantially as depicted in FIG. 4, and relevant data are as follows: $^1$H NMR (400 MHz, DMSO) δ 9.54 (d, J=31.2 Hz, 2H), 8.49 (d, J=2.2 Hz, 1H), 8.39 (dd, J=9.0, 2.2 Hz, 1H), 8.14 (d, J=7.5 Hz, 1H), 8.05 (d, J=7.6 Hz, 1H), 7.55 (dd, J=8.5, 6.0 Hz, 2H), 5.31 (t, J=5.0 Hz, 1H), 5.07-4.81 (m, 2H), 3.84-3.66 (m, 2H), 3.59-3.43 (m, 1H), 3.31-3.15 (m, 1H), 3.03 (d, J=22.5 Hz, 2H), 2.64-2.44 (m, 1H), 2.38-2.24 (m, 1H), 1.39 (d, J=6.0 Hz, 6H).

TABLE 2

| 2Theta | d Spacing | Relative Intensity % |
|---|---|---|
| 3.90 | 22.66 | 82.52 |
| 5.83 | 15.16 | 49.50 |
| 7.78 | 11.36 | 95.14 |
| 9.77 | 9.05 | 18.03 |
| 11.71 | 7.56 | 29.74 |
| 12.83 | 6.90 | 26.10 |
| 13.67 | 6.48 | 31.07 |
| 14.20 | 6.24 | 38.94 |
| 14.61 | 6.06 | 31.92 |
| 15.62 | 5.67 | 16.16 |
| 17.20 | 5.15 | 11.10 |
| 18.26 | 4.86 | 11.09 |
| 19.13 | 4.64 | 45.87 |
| 19.63 | 4.52 | 100.00 |
| 20.70 | 4.29 | 24.09 |
| 21.24 | 4.18 | 41.26 |
| 22.27 | 3.99 | 18.51 |
| 22.85 | 3.89 | 28.99 |
| 23.28 | 3.82 | 23.29 |
| 24.44 | 3.64 | 47.51 |
| 24.93 | 3.57 | 41.07 |
| 25.60 | 3.48 | 14.86 |
| 27.42 | 3.25 | 18.32 |
| 27.81 | 3.21 | 21.56 |
| 28.35 | 3.15 | 22.01 |
| 29.57 | 3.02 | 23.44 |
| 30.10 | 2.97 | 25.93 |
| 31.35 | 2.85 | 14.86 |
| 31.88 | 2.81 | 9.34 |
| 32.78 | 2.73 | 4.26 |
| 33.69 | 2.66 | 4.06 |
| 35.68 | 2.52 | 10.65 |
| 37.74 | 2.38 | 5.21 |

Example 2

Figure 5:
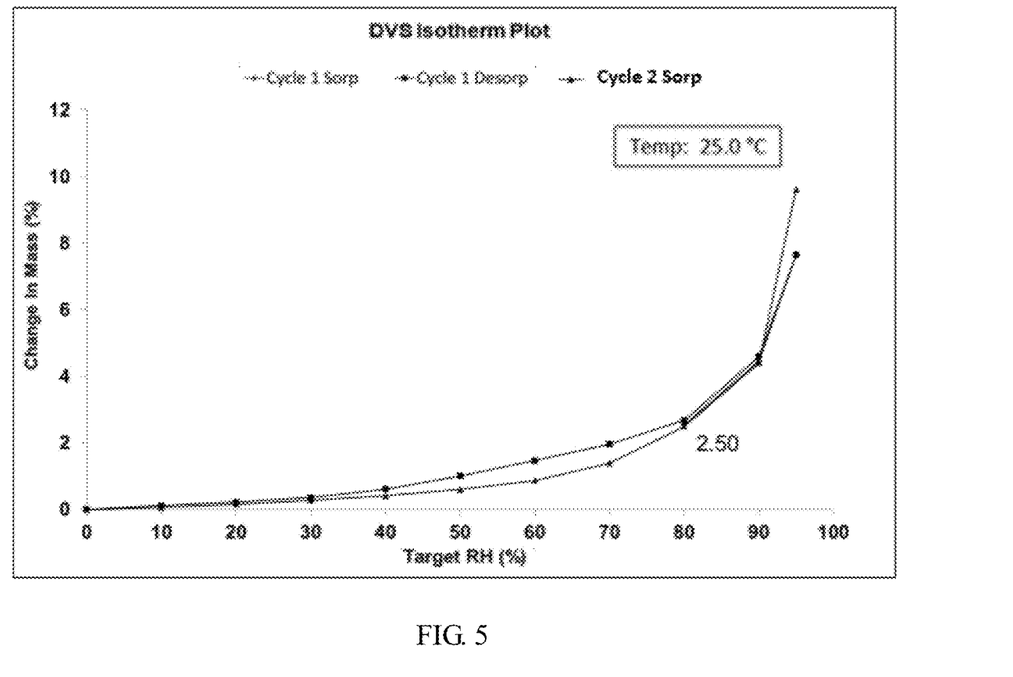
FIG. 5 shows a DVS plot of Form CS3 in Example 2

Hygroscopicity Assessment of Form CS3 of Ozanimod Hydrochloride:

Dynamic vapor sorption (DVS) was applied to test hygroscopicity of Form CS3 with about 10 mg of sample. The result is listed in Table 3. The DVS plot is substantially as depicted in FIG. 5.

TABLE 3

| Solid Form | Weight Gain under 80% RH |
|---|---|
| Form CS3 of ozanimod hydrochloride | 2.50% |

The result indicates that the weight gain of Form CS3 under 80% RH is 2.50%. According to the definition of hygroscopicity, Form CS3 is hygroscopic. The low hygroscopicity meets the requirement of medicine.

Description and definition of hygroscopicity (Chinese Pharmacopoeia 2015 edition appendix Drug hygroscopic test guidelines, test at 25° C.+/−1° C., 80% RH).

deliquescent: Sufficient water is absorbed to form a liquid;

very hygroscopic: Increase in mass is equal to or greater than 15%;

hygroscopic: Increase in mass is less than 15% and equal to or greater than 2%;

slightly hygroscopic: Increase in mass is less than 2% and equal to or greater than 0.2%.

no or almost no hygroscopic: Increase in mass is less than 0.2%.

Example 3

Solubility Assessment of Form CS3 of Ozanimod Hydrochloride:

Form CS3 of ozanimod hydrochloride was suspended into SGF (Simulated gastric fluids, pH=1.8), FeSSIF (Fed state simulated intestinal fluids, pH=5.0) and water to obtain saturated solutions. After being equilibrated for 1 h, 4 h and 24 h, concentrations of the saturated solutions were measured by HPLC. The results are listed in Table 4.

TABLE 4

| Time (h) | Solubility (mg/mL) | | |
|---|---|---|---|
| | SGF | FeSSIF | $H_2O$ |
| 1 | 0.2 | 2.1 | 1.1 |
| 4 | 0.2 | 2.1 | 1.4 |
| 24 | 0.2 | 1.8 | 1.3 |

The results show that Form CS3 of ozanimod hydrochloride has good solubility in SGF, FeSSIF and $H_2O$, which is beneficial to improve the bioavailability of the drug. Solubility is one of the key properties of drugs, which affects drug absorption in body directly. As the solubility of different crystalline drugs may be obviously different, the absorption dynamic in body may change, which results in the difference in bioavailability and ultimately affects the clinical safety and efficacy of drugs. Therefore, Form CS3 of ozanimod hydrochloride of the present disclosure has superior effects in solubility.

Example 4

Particle Size Distribution and Morphology Study:

Sample of Form CS3 was taken for particle size distribution test. The results are shown in Table 5.

TABLE 5

| Solid Form | MV(μm) | SD | D10 (μm) | D50 (μm) | D90 (μm) |
|---|---|---|---|---|---|
| Form CS3 of ozanimod hydrochloride | 131.8 | 107.7 | 19.94 | 100.5 | 287.0 |

The abbreviations used in the invention are explained as follows:

Mv: Average particle size calculated by volume.

D10: particle size which accounts for 10% of the particle size distribution (volume distribution).

D50: particle size which accounts for 50% of the particle size distribution (volume distribution), also known as the median diameter.

D90: particle size which accounts for 90% of the particle size distribution (volume distribution).

Figure 6:
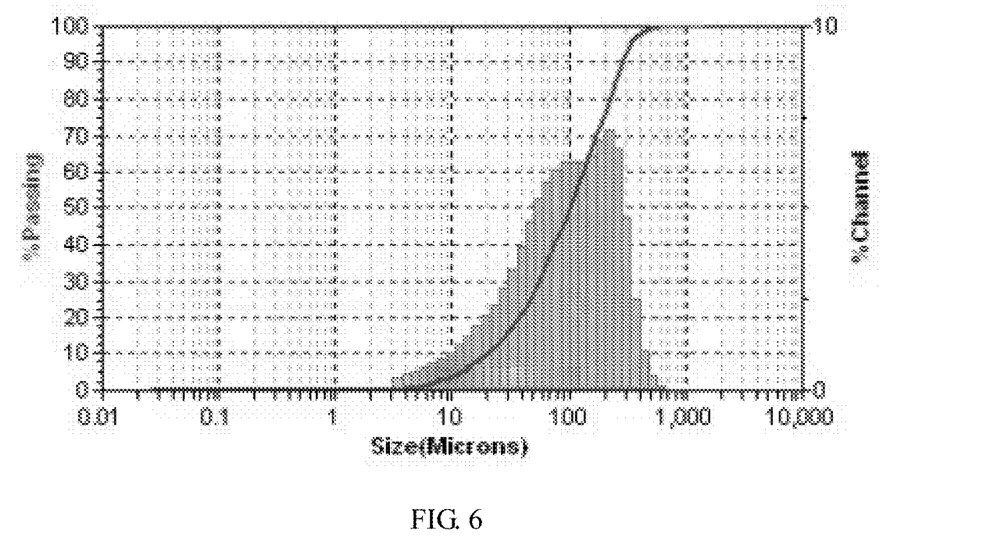
FIG. 6 shows a PSD diagram of Form CS3 in Example 4
Figure 7:
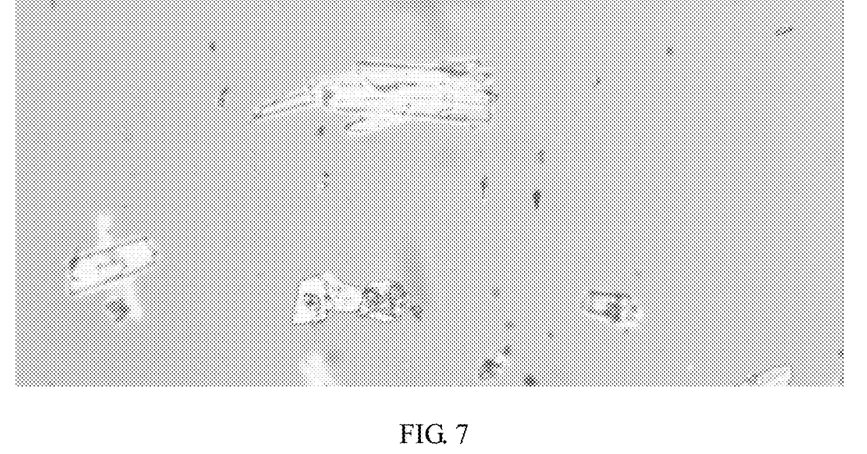
FIG. 7 shows a PLM image of Form CS3 in Example 4

The particle size distribution (PSD) diagram and polarized Light microscopy (PLM) image of Form CS3 are substantially as depicted in FIG. 6 and FIG. 7. The result shows that the average particle size of Form CS3 is 131.8 and the particle size distribution is narrow and uniform, which presents an almost normal distribution. Furthermore, the PLM image shows that Form CS3 is flaky with good dispersion.

Example 5

Figure 8:
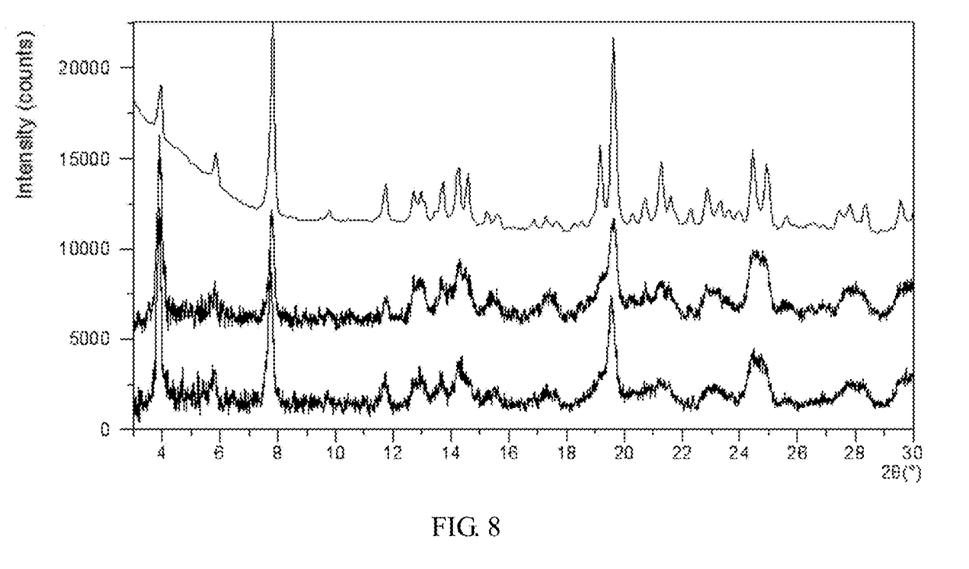
FIG. 8 shows an XRPD pattern overlay of Form CS3 before and after stability assessment in Example 5

Stability Assessment of Form CS3 of Ozanimod Hydrochloride:

Two samples of Form CS3 of ozanimod hydrochloride were placed in constant temperature and humidity chambers at 25° C./60% RH and 40° C./75% RH for 2 weeks. XRPD was used to test the crystalline form. The XRPD overlay pattern is substantially as depicted in FIG. 8 (from top to bottom: XRPD pattern of Form CS3 before and after being stored under 25° C./60% RH and 40° C./75% RH for 2 weeks). No form change was observed for Form CS3 after being stored at 25° C./60% RH and 40° C./75% RH for 2 weeks. It can be seen that Form CS3 of ozanimod hydrochloride has good stability, which is benefit for drug storage.

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

What is claimed is:

1. A crystalline form CS3 of ozanimod hydrochloride, wherein the X-ray powder diffraction pattern shows characteristic peaks at 2 theta values of 19.6°±0.2°, 24.9°±0.2° and 5.8°±0.2° using CuKα radiation.

2. The crystalline form CS3 of ozanimod hydrochloride according to claim 1, wherein the X-ray powder diffraction pattern shows one or two or three characteristic peaks at 2 theta values of 7.8°±0.2°, 11.7°±0.2° and 29.5°±0.2° using CuKα radiation.

3. The crystalline form CS3 of ozanimod hydrochloride according to claim 1, wherein the X-ray powder diffraction pattern shows one or two or three characteristic peaks at 2 theta values of 3.9°±0.2°, 14.2°±0.2° and 20.7°±0.2° using CuKα radiation.

4. A process for preparing crystalline form CS3 of ozanimod hydrochloride according to claim 1, wherein the process comprises:
   dissolving ozanimod hydrochloride into ethanol or a mixture of solvents selected from an alcohol and an arene, an alcohol and a nitrile, an alcohol and an acid, an acid and water,
   filtering and adding a polymer into the solution and then evaporating at room temperature to obtain a white solid.

5. The process for preparing crystalline form CS3 of ozanimod hydrochloride according to claim 4, wherein each said alcohol is methanol or ethanol; each said acid is acetic acid; said arene is toluene; said nitrile is acetonitrile.

6. A pharmaceutical composition, wherein said pharmaceutical composition comprises a therapeutically effective amount of crystalline form CS3 of ozanimod hydrochloride according to claim 1 and a pharmaceutically acceptable carrier, a diluent or an excipient.

7. A method for treating ulcerative colitis, comprising administering to a patient in need thereof a therapeutically effective amount of the crystalline form CS3 of ozanimod hydrochloride according to claim 1.

8. A method for treating multiple sclerosis, comprising administering to a patient in need thereof a therapeutically effective amount of the crystalline form CS3 of ozanimod hydrochloride according to claim 1.

9. The crystalline form CS3 of ozanimod hydrochloride according to claim 2, wherein the X-ray powder diffraction pattern shows one or two or three characteristic peaks at 2 theta values of 3.9°±0.2°, 14.2°±0.2° and 20.7°±0.2° using CuKα radiation.

10. A pharmaceutical composition, wherein said pharmaceutical composition comprises a therapeutically effective amount of crystalline form CS3 of ozanimod hydrochloride according to claim 9 and a pharmaceutically acceptable carrier, a diluent or an excipient.

11. A method for treating ulcerative colitis, comprising administering to a patient in need thereof a therapeutically effective amount of the crystalline form CS3 of ozanimod hydrochloride according to claim 9.

12. A method for treating multiple sclerosis, comprising administering to a patient in need thereof a therapeutically effective amount of the crystalline form CS3 of ozanimod hydrochloride according to claim 9.

\* \* \* \* \*